US009993599B2

(12) United States Patent
Andreoni

(10) Patent No.: US 9,993,599 B2
(45) Date of Patent: Jun. 12, 2018

(54) SKIN ENGAGEMENT MEMBER FOR USE WITH NEEDLE ASSEMBLY OR MEDICAL INJECTOR

(75) Inventor: Todd Ryan Andreoni, Lyndhurst, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1317 days.

(21) Appl. No.: 12/861,258

(22) Filed: Aug. 23, 2010

(65) Prior Publication Data

US 2012/0046614 A1 Feb. 23, 2012

(51) Int. Cl.
*A61M 5/32* (2006.01)
*A61M 5/42* (2006.01)
*A61M 5/46* (2006.01)

(52) U.S. Cl.
CPC ........ *A61M 5/3287* (2013.01); *A61M 5/3243* (2013.01); *A61M 5/326* (2013.01); *A61M 5/3293* (2013.01); *A61M 5/422* (2013.01); *A61M 5/46* (2013.01); *A61M 2005/3267* (2013.01)

(58) Field of Classification Search
CPC .. A61M 5/3243; A61M 5/3245; A61M 5/326; A61M 5/3287; A61M 5/422; A61M 2005/3267
USPC ................................ 604/117, 192, 197, 198
See application file for complete search history.

(56) References Cited

U.S. PATENT DOCUMENTS

| 4,883,473 | A | 11/1989 | Thomas |
| 4,955,871 | A | 9/1990 | Thomas |
| 5,015,234 | A * | 5/1991 | Jullien .......................... 604/110 |
| 5,295,965 | A | 3/1994 | Wilmot |
| 5,599,309 | A | 2/1997 | Marshall et al. |
| 5,634,906 | A | 6/1997 | Haber et al. |
| 5,944,700 | A * | 8/1999 | Nguyen et al. ................ 604/263 |
| 5,984,899 | A | 11/1999 | D'Alessio et al. |
| 6,569,115 | B1 | 5/2003 | Barker et al. |
| 7,309,326 | B2 | 12/2007 | Fangrow, Jr. |
| 7,540,858 | B2 | 6/2009 | DiBiasi |
| 7,645,265 | B2 | 1/2010 | Stamp |
| 7,670,314 | B2 | 3/2010 | Wall et al. |
| 7,981,085 | B2 | 7/2011 | Ethelfeld |
| 2003/0171715 | A1 | 9/2003 | Hommann |
| 2003/0212362 | A1 | 11/2003 | Roser |

(Continued)

FOREIGN PATENT DOCUMENTS

| EP | 1 949 928 A1 | 1/2008 |
| GB | 2 463 034 A | 3/2010 |
| JP | 2006-341095 A | 12/2006 |

(Continued)

*Primary Examiner* — Shefali Patel

(74) *Attorney, Agent, or Firm* — Dickinson Wright PLLC

(57) ABSTRACT

A skin engagement member is provided herein for use with a needle assembly or a medical injector to minimize irritation of a patient's skin surrounding an injection site during injection by a needle of the needle assembly or the medical injector. The skin engagement member includes: a body; a surface defined on the body for engaging the patient's skin during injection by the needle; an aperture formed through the body configured to permit passage therethrough of the needle; and, rotatable mounting features for rotatably mounting the body to the needle assembly or the medical injector such that the surface, while engaging the patient's skin, is rotatable about the aperture.

18 Claims, 1 Drawing Sheet

(56) References Cited

U.S. PATENT DOCUMENTS

2006/0276747 A1* 12/2006 Moos et al. .................. 604/117
2008/0177235 A1* 7/2008 DiBiasi ........................ 604/192

FOREIGN PATENT DOCUMENTS

| JP | 2007-511325 A | 5/2007 |
| JP | 2008-246190 A | 10/2008 |
| WO | 2009040602 A1 | 4/2009 |
| WO | 2009/139857 A1 | 11/2009 |
| WO | 2010035056 A1 | 4/2010 |

* cited by examiner

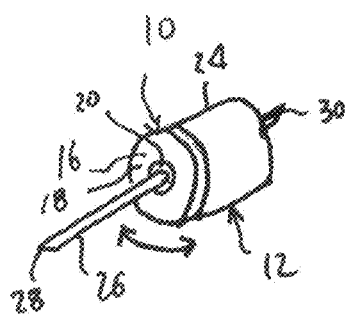
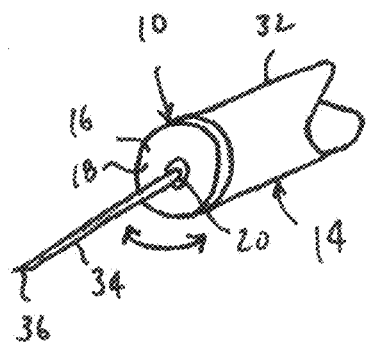
FIG. 1
FIG. 2
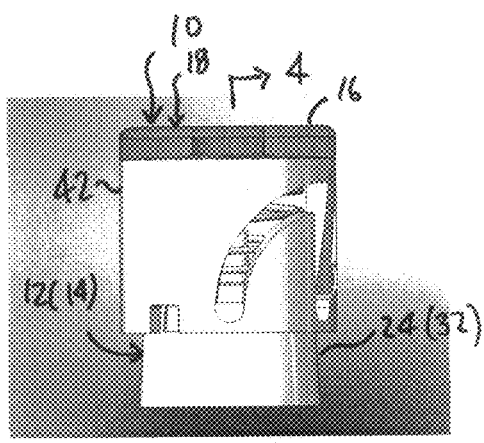
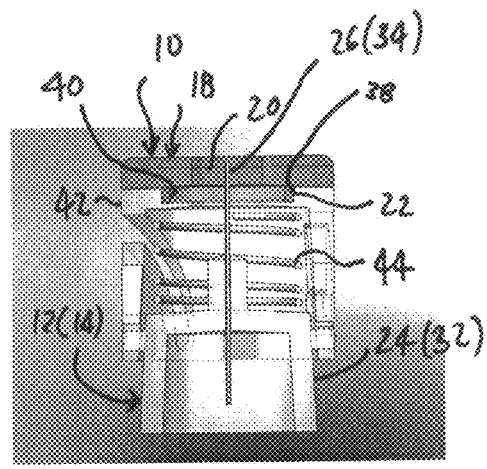
FIG. 3
FIG. 4

SKIN ENGAGEMENT MEMBER FOR USE WITH NEEDLE ASSEMBLY OR MEDICAL INJECTOR

FIELD OF THE INVENTION

This invention relates to a skin engagement member for use with a needle assembly or a medical injector to minimize irritation of a patient's skin surrounding an injection site during injection.

BACKGROUND OF THE INVENTION

Certain medical injectors are known to engage a patient's skin during injection. For example, a pen injector is typically caused to press against a patient's skin so as to ensure proper insertion of the injection needle. The patient's skin may act as a stop to ensure proper injection depth and/or to provide stability during injection.

With engagement of the patient's skin, portions of the patient's skin surrounding the injection site may be irritated by relative movement thereagainst. For example, certain needle shields are caused to activate passively during injection, with the needle shield being rotatably displaced against the patient's skin. Upon withdrawal of the needle after injection, the activated needle shield is caused to assume a shielding position. The rotation, however, of the shield against the patient's skin may cause discomfort or irritation.

SUMMARY OF THE INVENTION

A skin engagement member is provided herein for use with a needle assembly or a medical injector to minimize irritation of a patient's skin surrounding an injection site during injection by a needle of the needle assembly or medical injector. The skin engagement member includes: a body; a surface defined on the body for engaging the patient's skin during injection by the needle; an aperture formed through the body configured to permit passage therethrough of the needle; and, rotatable mounting features for rotatably mounting the body to the needle assembly or medical injector such that the surface, while engaging the patient's skin, is rotatable about the aperture. Advantageously, with the subject invention, a skin engagement member may be located in engagement with a patient's skin which, due to pressure applied during injection, may be held in a generally fixed position against the skin with rotation of the injector about the skin engagement member being permitted. Accordingly, irritation of the patient's skin about the injection site may be minimized.

These and other features of the invention will be better understood through a study of the following detailed description and accompanying drawings.

BRIEF DESCRIPTION OF THE DRAWINGS

FIG. 1 is a perspective view of a needle assembly formed in accordance with the subject invention;

FIG. 2 is a partial perspective view of a medical injector formed in accordance with the subject invention;

FIG. 3 is a side elevational view showing the subject invention in use with a shield; and, FIG. 4 is a cross-sectional view taken along line 4-4 of FIG. 3.

DETAILED DESCRIPTION OF THE INVENTION

With reference to the Figures, a skin engagement member is shown and generally designated with the reference numeral 10. The skin engagement member 10 is useable with a needle assembly 12 or a medical injector 14 to minimize irritation of a patient's skin surrounding an injection site during injection by a needle of the needle assembly 12 or the medical injector 14. The skin engagement member 10 generally includes: a body 16; a surface 18 defined on the body 16 for engaging a patient's skin during injection; an aperture 20 formed through the body 16 configured to permit passage therethrough of a needle; and, rotatable mounting features 22 for rotatably mounting the body 16 to the needle assembly 12 or the medical injector 14 such that the surface 18 is rotatable about the aperture 20.

Due to the rotatability of the body 16, the skin engagement member 10 may act to minimize irritation of a patient's skin surrounding an injection site during injection.

As will be appreciated by those skilled in the art, the needle assembly 12 may be of any known configuration. By way of non-limiting example, the needle assembly 12 may include a hub 24 to which is attached a needle 26 having a distal end 28 formed for insertion into a patient. The hub 24 may include features for mounting onto an injector, such as a pen injector. The body 16 may be rotatably mounted to the hub 24. In addition, the needle 26 extends through the aperture 20 so as to have the distal end 28 exposed. It is preferred that a sufficient length of the needle 26 is exposed to permit proper depth for injection. In addition, the surface 18 is formed to generally face in the same direction away from the hub 24 as the distal end 28 of the needle 26. As shown schematically in FIG. 1, the surface 18 is formed to be rotatable about the aperture 20, thus, permitting the body 16 to be rotatable about the needle 26. Proximal end 30 of the needle 26 may be formed as necessary to suit a particular application.

The medical injector 14 may be of any known type. The medical injector 14 may include a barrel 32 from which extends needle 34 having a distal end 36 formed for insertion into a patient. The body 16 may be rotatably mounted to the barrel 32, either directly or indirectly. For example, the body 16 may be mounted indirectly to the barrel 32, by being mounted on the needle assembly 12 which, in turn, is mounted to the barrel 32. As with the needle assembly 12, the needle 34 extends distally from the body 16, particularly the surface 18, to preferably have sufficient length for proper injection depth. The surface 18 preferably generally faces the same direction as the distal end 36 away from the barrel 32. As shown schematically in FIG. 2, the surface 18 is configured to rotate about the aperture 20, thus, permitting rotation of the body 16 about the needle 34.

During an injection, the skin engagement member 10 may be caused to come into contact with the patient's skin. The skin engagement member 10 may act as a stop to ensure proper injection depth and/or to provide stability during an injection. With this arrangement, the surface 18 will be in contact with the patient's skin. With the needle 26, 34 being at proper injection depth, an injection may be caused to be administered as is known in the art. With pressure being applied to the surface 18 during injection, any relative movement or displacement of the needle assembly 12 or the medical injector 14 may result in rotation relative to the body 16 with the body 16 being held generally fixed relative to the patient's skin. With the body 16 being held generally fixed, irritation of the patient's skin can be minimized about the injection site.

The body 16 may be formed with various shapes and dimensions, but is preferably disc-shaped. The surface 18 is preferably formed to define a stable resting surface against a patient's skin. Preferably, the surface 18 is planar. It is also preferred that the aperture 20 be centrally located on the body 16 so as to provide a central axis of rotation.

The rotatable mounting features 22 may be of any known configuration for fixing the body 16 to the needle assembly 12 or the medical injector 14 so as to permit relative rotation therebetween. By way of non-limiting example, with reference to FIG. 4, a mounting hole 38 may be formed in the needle assembly 12 (e.g., the hub 24) or the medical injector 14 formed to cooperate with one or more snap fingers 40 which protrude from the body 16. The snap fingers 40 are formed to engage the mounting hole 38 so as to be axially fixed relative thereto with relative rotation being permitted. As will be appreciated by those skilled in the art, other forms of rotatable mounting are useable with the subject invention.

The needle assembly 12 or the medical injector 14 may be provided with a shield 42 for selectively covering the distal end 28, 36 of the needle 26, 34. As will be appreciated by those skilled in the art, the shield 42 may be configured in any manner consistent with the subject invention. By way of non-limiting example, the shield 42 may be formed to be axially displaceable along the length of the needle assembly 12 or the medical injector 14, e.g., being axially displaceable relative to the hub 24 or the barrel 32. A spring 44, or other drive element, may be also provided to generate driving force for selectively displacing the shield 42. The body 16 may be rotatably mounted to the shield 42 in the same manner as described above.

The shield 42 may be rotatably displaceable during use. For example, during injection, the shield 42 may be caused to rotate relative to the hub 24 or the barrel 32, e.g., to be activated. The body 16 permits rotation of the shield 42 without such rotational movement being applied to the patient's skin. Rather, the shield 42 may be caused to rotate relative to the body 16 with the body 16 being held generally fixed relative to the patient's skin

What is claimed is:

1. A skin engagement member for use with a needle assembly or a medical injector to minimize irritation of a patient's skin surrounding an injection site, the needle assembly or the medical injector including a body member, a needle extending from the body member and a shield for selectively covering a distal end of the needle, wherein the shield is movable relative to a distal end of the body member, said skin engagement member comprising:
    a body;
    a surface defined on said body for engaging the patient's skin during injection by the needle;
    an aperture formed through said body configured to permit passage therethrough of the needle; and
    rotatable mounting features for rotatably mounting said body to said shield to permit relative rotation therebetween about said aperture with the needle passing through said aperture, wherein the body is axially fixed relative to the shield.

2. The skin engagement member as in claim 1, wherein said surface is generally planar.

3. The skin engagement member as in claim 1, wherein said aperture is centrally located on said body.

4. The skin engagement member as in claim 1, wherein said mourning features include at least one protruding snap finger formed to snap engage an opening formed in the needle assembly or the medical injector.

5. The skin engagement member as in claim 1, wherein said shield is rotatably displaceable relative to the body member.

6. The skin engagement member as in claim 1, wherein the needle passes through said aperture.

7. The skin engagement member as in claim 1, wherein the shield is axially displaceable relative to the body member.

8. The skin engagement member as in claim 1, wherein the shield includes a drive element to generate a driving force for moving the shield.

9. The skin engagement member as in claim 8, wherein the drive element comprises a spring.

10. The skin engagement member as in claim 9, wherein the surface is generally planar.

11. The skin engagement member as in claim 9, wherein the aperture is centrally located on the body.

12. The skin engagement member as in claim 9, wherein the mounting features include at least one protruding snap finger formed to snap engage an opening formed in the needle assembly or the medical injector.

13. The skin engagement member as in claim 9, wherein the shield is rotatably displaceable relative to the body member.

14. A skin engagement member for use with a needle assembly or a medical injector, wherein the needle assembly or the medical injector includes a body member, a needle extending from the body member and a shield movable relative to a distal end of the body member for selectively covering a distal end of the needle, the skin engagement member comprising:
    a body having an engaging surface for engaging a patient's skin during injection by the needle, the body having an aperture formed therethrough, the aperture being configured to permit passage of the needle therethrough;
    wherein the skin engagement member includes rotatable mounting features for rotatably mounting the body to the shield to permit relative rotation therebetween about the aperture with the needle passing through said aperture; and
    wherein the body is axially fixed relative to the shield.

15. The skin engagement member as in claim 14, wherein the shield is axially displaceable relative to the body member.

16. The skin engagement member as in claim 15, wherein a drive element comprises a spring.

17. The skin engagement member as in claim 14, wherein the needle passes through said aperture.

18. The skin engagement member as in claim 14, wherein the shield includes a drive element to generate a driving force for moving the shield.

* * * * *